United States Patent [19]

Samain et al.

[11] Patent Number: 5,496,377
[45] Date of Patent: Mar. 5, 1996

[54] PROCESS FOR THE DIRECT DYEING OF KERATINOUS FIBRES USING WATER VAPOR

[75] Inventors: Henri Samain, Bievres; Jean-Michel Sturla, Saint-Cloud, both of France

[73] Assignee: L'Oreal, Paris, France

[21] Appl. No.: 357,371

[22] Filed: Dec. 16, 1994

[30] Foreign Application Priority Data

Dec. 22, 1993 [FR] France ................... 93 15485

[51] Int. Cl.$^6$ ................... A61K 7/13
[52] U.S. Cl. ................... 8/414; 8/405; 8/415; 8/421; 132/208
[58] Field of Search ................... 8/404, 405, 414, 8/415, 421; 132/208

[56] References Cited

U.S. PATENT DOCUMENTS

| | | | |
|---|---|---|---|
| 2,750,326 | 6/1956 | Eckardt et al. | 8/415 |
| 3,274,249 | 9/1966 | Brunner et al. | 8/415 |
| 3,488,138 | 1/1970 | Iscowitz | 8/414 |
| 3,629,330 | 12/1971 | Brody et al. | 8/414 |
| 4,125,601 | 11/1978 | Bugaut et al. | 8/414 |
| 4,166,473 | 9/1979 | Bauer et al. | 132/9 |
| 4,330,291 | 5/1982 | Bugaut et al. | 8/414 |
| 4,341,229 | 7/1982 | Bauer et al. | 132/7 |
| 4,511,360 | 4/1985 | Monnais et al. | 8/414 |
| 4,573,378 | 3/1986 | Seidel et al. | 8/414 |
| 4,601,726 | 7/1986 | Grollier et al. | 8/414 |
| 4,725,283 | 2/1988 | Cotteret et al. | 8/414 |
| 4,834,768 | 5/1989 | Grollier | 8/414 |
| 4,935,032 | 6/1990 | Grollier | 8/414 |
| 4,981,486 | 1/1991 | Grollier et al. | 8/414 |
| 5,067,966 | 11/1991 | Mager et al. | 8/414 |
| 5,104,413 | 4/1992 | Ikeda | 8/405 |

FOREIGN PATENT DOCUMENTS

| | | |
|---|---|---|
| 103547 | 3/1984 | European Pat. Off. . |
| 312343 | 4/1989 | European Pat. Off. . |
| 2273492 | 1/1976 | France . |
| 4235436 | 4/1993 | Germany . |
| 61-143315 | 7/1986 | Japan . |
| 741334 | 11/1955 | United Kingdom . |
| 2168082 | 6/1986 | United Kingdom . |

OTHER PUBLICATIONS

*The Chemistry of Synthetic Dyes*, vol. V, Academic Press, 1971, pp. 508–518.

*Primary Examiner*—Paul Lieberman
*Assistant Examiner*—Caroline L. Dusheck
*Attorney, Agent, or Firm*—Finnegan, Henderson, Farabow, Garrett & Dunner

[57] ABSTRACT

A process for the direct dyeing (or colouring) of keratinous fibres, in particular human keratinous fibres, comprising the step of: directly dyeing the fibres by contacting the fibres (1) with a composition containing at least one direct dye chosen from specific 2-nitro-para-phenylenediamine derivatives and/or nitro derivatives of specific aminophenols, and (2) with a gas containing water vapour, the temperature of the gas being at least 75° C. and the contact time between the gas and the fibres to be dyed not exceeding two minutes. The hair is dyed uniformly over the whole head of hair, from the roots to the ends, regardless of the condition of the hair.

28 Claims, No Drawings

PROCESS FOR THE DIRECT DYEING OF KERATINOUS FIBRES USING WATER VAPOR

The present invention is directed to a process for the direct dyeing (or colouring) of keratinous fibres, in particular human keratinous fibres such as hair, using water vapour and a composition comprising specific direct dyes.

It is well known in the field of hair dyeing to use so-called oxidation dyes which lead to shades which cover the hair very well and have very good hold. An oxidation dye nevertheless requires the use of oxidizing agents that can, in the long run, damage the hair when such dyes are applied frequently. With the object of obtaining dyes which, although they have less hold, are less degrading to the hair, so-called direct dyes have been used. Direct dyes are dyes which do not use an oxidation mechanism and which are capable in themselves of dyeing the keratinous fibres.

By virtue of the variety of substances which can be used, direct dyes enable a wide spectrum of shades to be obtained, ranging from yellow to blue via red. Among direct dyes, there may be mentioned the nitro benzenic dyes which have high performance and are generally well tolerated. In hair dyeing, blue shades are necessary as components which enable natural shades to be obtained. It has been proposed to use 2-nitro-para-phenylenediamine derivatives in which the amino group in position 4 is disubstituted and the amino group in position 1 is being monosubstituted as blue direct hair dyes. In order to obtain shades with glints, the nitro aminophenol derivatives are preferably used. However, these two classes of dyes have the disadvantage of being very selective with regard to the fibres to be dyed.

The selectivity of a dye is defined as the difference in uptake, or dyeing power, of the dye on the hair fibre. The selectivity depends on whether the hair has been sensitized to a greater or lesser extent, i.e., "damaged," either by a treatment such as bleaching or permanent waving, or by atmospheric agents, especially in the case of the ends of the hair. Thus, generally speaking, the direct dyes discussed above are taken up better on slightly sensitized or damaged hair than on natural hair.

The consequence of this selectivity problem is the de-equilibration of the shades or the glints on the hair, depending on the degree of sensitization, i.e., the state of degradation of the hair, on which the composition containing the dyes is applied. The dyeing results obtained on hair which has different degrees of sensitization are thus heterogeneous. Such irregularities are obviously not desirable from an aesthetic point of view. The present invention aims to resolve this problem.

It has been discovered, surprisingly, that the use of a gas comprising water vapour, heated to a temperature of at least 75° C., preferably greater than 75° C., on hair treated with certain direct dyes, enables dyeing results to be obtained which show little or no dependence on the degree of sensitization of the keratinous fibres being dyed. According to the present invention, the hair is thus dyed uniformly over the whole head of hair, from the roots to the ends, regardless of the condition of the hair.

It will be noted that the use of water vapour in various hair treatment processes has been described in French Patent Application No. 2,273,492 and its English language counterparts, U.S. Pat. Nos. 4,217,914, 4,422,853, 4,948,579 and 5,196,189, the disclosures of which are incorporated by reference, in which documents water vapour which was heated to approximately 100°–150° C. was used to accelerate or bring about chemical reactions of compounds which were already placed on the hair. One example of direct hair dyeing therein thus describes the use of 2-nitro-para-phenylenediamine. However, the selectivity, as previously defined, of the direct dye was not reduced when a water vapour process was employed, and thus such a dye was excluded from the scope of the present invention.

The present invention is thus directed to a process for the direct dyeing of keratinous fibres, in particular human keratinous fibres, comprising the step of: directly dyeing the fibres, the fibres having previously been contacted with a composition containing at least one direct dye selected from the 2-nitro-para-phenylene-diamine derivatives of formula (I), discussed below, and/or the nitro aminophenol derivatives of formula (II), also discussed below, by contacting the fibres with a gas containing water vapour, the temperature of the gas being greater than 75° C., for a contact time between the gas and the fibres to be dyed less than two minutes.

The present invention further contemplates a process for the direct dyeing of keratinous fibres, comprising the step of: directly dyeing the fibres by contacting the fibres (1) with a composition containing at least one direct dye selected from the 2-nitro-para-phenylene-diamine derivatives of formula (I), discussed below, and/or the nitro aminophenol derivatives of formula (II), also discussed below, and (2) with a gas containing water vapour, the temperature of the gas and the contact time between the gas and the fibres being sufficient to substantially uniformly dye the fibres.

The present invention is also directed to a process for the direct dyeing of keratinous fibres, comprising the step of: directly dyeing the fibres by contacting the fibres (1) with a composition containing at least one direct dye selected from the 2-nitro-para-phenylene-diamine derivatives of formula (I), discussed below, and/or the nitro aminophenol derivatives of formula (II), also discussed below, and (2) with a gas containing water vapour, the temperature of the gas being at least 75° C. and the contact time between the gas and the fibres being sufficient to substantially uniformly dye the fibres.

A further embodiment of the present invention includes a process for the direct dyeing of keratinous fibres which comprises the step of: directly dyeing the fibres (1) with a composition containing at least one direct dye selected from the 2-nitro-para-phenylene-diamine derivatives of formula (I), discussed below, and/or the nitro aminophenol derivatives of formula (II), also discussed below, and (2) with a gas containing water vapour, for a time not exceeding two minutes, and wherein the gas has a temperature sufficient to substantially uniformly dye the fibres.

A still further embodiment contemplated by the present invention is a process for the direct dyeing of keratinous fibres, in particular human keratinous fibres such as hair, comprising the step of: directly dyeing the fibres by contacting the fibres (1) with a composition containing at least one direct dye selected from the 2-nitro-para-phenylenediamine derivatives of formula (I), discussed below, and/or the nitro aminophenol derivatives of formula (II), also discussed below, and (2) with a gas containing water vapour, the temperature of the gas being at least 75° C., and the contact time between the gas and the fibres to be dyed not exceeding two minutes.

The process of the present invention is used for the direct dyeing of keratinous fibres in general. The preferred form of keratinous fibres taught by the present invention is human keratinous fibres.

The direct dyes which are suitable for the invention correspond to the following formulae (I) and (II):

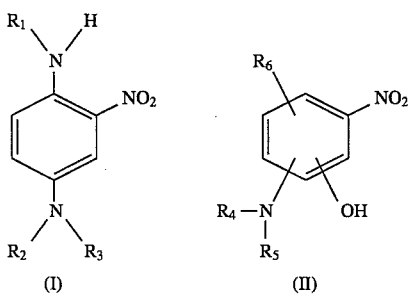

(I)          (II)

in which:

$R_1$ is selected from $C_1$-$C_4$ alkyl, $C_2$-$C_4$ monohydroxyalkyl, $C_2$-$C_4$ polyhydroxyalkyl radicals, $C_1$-$C_4$ ($C_1$-$C_4$ alkoxy) alkyl radicals and ($C_1$-$C_4$) aminoalkyl radicals; $R_2$ and $R_3$ are selected from $C_1$-$C_4$ alkyl, $C_2$-$C_4$ monohydroxyalkyl and $C_2$-$C_4$ polyhydroxyalkyl radicals; $R_4$ and $R_5$ are selected from hydrogen, $C_1$-$C_4$ alkyl, $C_2$-$C_4$ monohydroxyalkyl, $C_2$-$C_4$ polyhydroxyalkyl and $C_1$-$C_4$ aminoalkyl radicals; and $R_6$ is selected from hydrogen, $C_1$-$C_4$ alkyl radicals, halogen atoms and an $NO_2$ group.

The dyes of formula (I) are preferably selected from the following compounds: N,N',N'-tris(2'-hydroxyethyl)-1,4-diamino-2-nitrobenzene, 1-methylamino-2-nitro-4-bis(2'-hydroxyethyl) aminobenzene, 1-methylamino-2-nitro-4-(N-methyl-N-2'-hydroxyethyl)aminobenzene, 1-(2'-aminoethyl)amino-2-nitro- 4-bis(2'-hydroxyethyl)amino- 4-(N-ethyl-N-2'-hydroxyethyl)amino- 1-(2'-hydroxyethyl)amino-2-nitrobenzene, 1-(2'-methoxyethyl)amino- 2-nitro-4-bis(2'-hydroxyethyl)aminobenzene, 1-(2',3'-dihydroxypropyl)amino-2-nitro-4-bis(2'-hydroxyethyl)aminobenzene, 1-(2',3'-dihydroxypropyl)amino-2-nitro- 4-(N-methyl N-2'-hydroxyethyl)aminobenzene, 1-(2',3'-dihydroxypropyl)amino- 2-nitro-4-(N-ethyl-N-2'-hydroxyethyl)aminobenzene, and 1-methylamino-2-nitro-4-(N-methyl-N- 2',3'-dihydroxypropyl)aminobenzene.

The dyes of formula (II) are preferably selected from the following compounds:

3-amino-4-hydroxynitrobenzene,
3-hydroxy-4-aminonitrobenzene,
2-hydroxy-3-amino-1,5-dinitrobenzene,
2-hydroxy-5-aminonitrobenzene,
1-hydroxy-3-nitro-4-N-(2'-hydroxyethyl)aminobenzene,
1-hydroxy-2-amino-3-nitrobenzene,
1-amino-2-nitro-4-hydroxy-5-methylbenzene,
1-N-(2'-hydroxyethyl)amino-2-hydroxy-4-nitrobenzene,
1-hydroxy-2-N-(2'-hydroxyethyl)amino-4,6-dinitrobenzene,
2-chloro-6-N-ethylamino-1-hydroxy-4-nitrobenzene,
6-chloro-4-nitro-2-aminophenol,
1-hydroxy-3-nitro-4-N-(3'-hydroxypropyl)aminobenzene,
1-hydroxy-2-N,N-(2'-hydroxyethyl)amino-5-nitrobenzene,
2-amino-4-hydroxy-1-nitrobenzene,
2-hydroxy-4-amino-1-nitrobenzene,
1-hydroxy-3-nitro-4-aminobenzene,
2-hydroxy-5-N-(2'-hydroxyethyl)amino-1-nitrobenzene,
2-hydroxy-6-amino-1-nitrobenzene,
2-hydroxy-3-amino-1-nitrobenzene,
2-hydroxy-3-chloro-6-amino-1-nitrobenzene,
2-N-(2'-hydroxyethyl)amino-3-hydroxy-1-nitrobenzene,
3-N-(2'-hydroxyethyl)amino-4-hydroxy-1-nitrobenzene,
2-hydroxy-6-N-(2'-hydroxyethyl)amino-1-nitrobenzene,
1-hydroxy-2,6-dinitro-4-methylaminobenzene,
2-N-(2'aminoethyl)amino-4-hydroxy-1-nitrobenzene,
3-hydroxy-4-N-(2'aminoethyl)amino-1-nitrobenzene and
2-N-(2'-hydroxyethylamino)-4-hydroxyl-1-nitrobenzene.

All of these dyes may be used in free form or in the form of salts such as hydrochloride, hydrobromide, sulphate and others. These dyes may be used alone or as mixtures. The direct dye or dyes of formula (I) and/or of formula (II) are preferably present in concentrations ranging from 0.01% to 10% by weight relative to the total weight of the dye composition.

The water vapour may be transported by a carrier gas that may additionally contain solvent vapour. As the vapour, gases such as oxygen and nitrogen, gas mixtures such as air or other vaporizable compounds can be used.

The solvents which may be used for the production of vapour are cosmetically acceptable organic solvents such as alcohols, glycols or glycol ethers. Suitable alcohols include ethanol, isopropanol, benzyl alcohol and phenethyl alcohol. Typical glycols or glycol ethers include the monomethyl, monoethyl and monobutyl ethers of ethylene glycol, propylene glycol, butylene glycol and dipropylene glycol, as well as alkyl ethers such as diethylene glycol monobutyl ether.

The gas preferably comprises at least 1% by volume of water vapour relative to the total volume of gas. The gas preferably contains either exclusively or essentially water vapour, or a mixture of water vapour and air. The temperature of the gas is at least 75° C., preferably greater than 75° C. The gas temperature is more preferably at least 85° C. and still more preferably ranges from 85° C. to 150° C. Still more preferably, the temperature of the gas ranges from 85° C. to less than 100° C. Most preferably the temperature of the gas ranges from 90° C. to less than 100° C.

During the process of the present invention, the gas is contacted with the fibres to be dyed for a period of time period preferably ranging from 0.01 second to less than 2 minutes. The gas is preferably contacted with the fibres for a period of time ranging from 0.01 second to 30 seconds and even more preferably from 1 to 10 seconds. Application of the gas may be repeated several times on the same fibres, with each application being conducted for a time period as prescribed above.

In a preferred embodiment of the process according to the invention, a hair dyeing composition containing the direct dyes of formula (I) and/or (II) is applied to the hair, and the hair is subsequently subjected to the action of the water vapour. Another embodiment of the present inventive process contemplates the dye composition and the gas comprising water vapour being applied simultaneously. It is also possible for all or some of the dye composition to be put onto the hair by means of the gas flow when some or all of the constituents of the formula can be entrained or vaporized. In a further embodiment of the invention, the application of water vapour is followed by rinsing with water.

The production of a hot gas comprising water vapour may be achieved using any apparatus known per se. An apparatus such as that described in French Patent Application No. 2,273,492 or its U.S. counterparts, U.S. Pat. Nos. 4,166,473 and 4,341,229, the disclosures of which, including the drawings, are incorporated by reference, or any other equivalent apparatus, is preferably used and is particularly suitable.

The dye composition used in the process according to the invention may be provided in forms usually used for dyeing hair, such as liquid which is thickened or gelled to a greater or lesser extent, cream, aerosol foam or any other form which is suitable for carrying out dyeing of hair.

The compositions used in accordance with the invention are generally aqueous compositions which may contain ingredients usually used in cosmetic compositions intended for dyeing hair, such as solvents, surface active agents, thickening agents, treating agents, basifying or acidifying agents, preserving agents, fragrances or any other additive used in this type of composition.

The dye composition containing at least one direct dye of formula (I) and/or (II) has a pH which generally ranges from 2 to 11.

The examples which follow illustrate the invention without limiting the scope of the invention.

EXAMPLE 1 (invention)

A composition having the following characteristics was used:

| | |
|---|---|
| 1-Hydroxy-3-nitro-4-N-(2'-hydroxyethyl)aminobenzene | 0.5 g |
| Propylene glycol monomethyl ether | 10 g |
| Coconut diethanolamide | 2 g |
| Oxyethylenated nonylphenol containing 9 mol of ethylene oxide | 8 g |
| 2-Amino-2-methyl-1-propanol qs | pH 9 |
| Water qs | 100 g |

The experimental procedure was as follows: the above composition was applied to natural hair and to the same hair which had been permanent waved. Two jets of water vapour at 90° C. were subsequently applied to the hair for 30 seconds each. The hair was rinsed with water and then dried.

The luminance L of the two types of hair treated with vapour was subsequently measured (measurements were made using a MINOLTA CHROMA METER CR 200 colorimeter).

The difference: L natural—L permanent waved, (ΔL), which represents the selectivity, was equal to 0.2. This value should be as low as possible since it represents the difference in colour between the two locks of hair.

EXAMPLE 2 (comparative)

The same composition as that of Example 1 was used. The experimental procedure was as follows: the above composition was applied to natural hair and to permanent waved hair, and the hair was left to stand for 30 minutes at room temperature. The hair was rinsed with water and then dried.

The difference: L natural—L permanent waved, (ΔL), which represents the selectivity, was equal to 4.8; it was much higher than that obtained with the process according to the invention (Ex. 1).

EXAMPLE 3 (invention)

A composition having the following characteristics was used:

| | |
|---|---|
| N,N',N'-tris(2-hydroxyethyl)-1,4-diamino-2-nitrobenzene | 0.5 g |
| Propylene glycol monomethyl ether | 10 g |
| Coconut diethanolamide | 8 g |
| 2-Amino-2-methyl-1-propanol qs | pH 9 |
| Water qs | 100 g |

The experimental procedure was as follows: the above composition was applied to natural hair and to the same hair permanent waved. Two jets of water vapour at 90° C. were subsequently applied to the hair for 30 seconds each. The hair was rinsed with water and then dried.

The luminance L of the two types of hair treated with vapour was subsequently measured (measurements were using a MINOLTA CHROMA METER CR 200 colorimeter).

The difference: L natural—L permanent waved, (ΔL), which represents the selectivity, was equal to 5.6.

EXAMPLE 4 (comparative)

The same composition as that of Example 3 was used. The experimental procedure was as follows: the above composition was applied to natural hair and to permanent waved hair, and the hair was left to stand for 30 minutes at room temperature. The hair was rinsed with water and then dried.

The difference: L natural—L permanent waved, (ΔL) which represents the selectivity, was equal to 11.8; it was twice as high as that obtained with the process according to the invention (Ex. 3).

EXAMPLE 5 (invention)

A composition having the following characteristics was used:

| | |
|---|---|
| 4-(N-Ethyl-N-2'-hydroxyethyl)amino-1-(2'-hydroxyethyl)amino-2-nitrobenzene | 0.5 g |
| Propylene glycol monomethyl ether | 10 g |
| Coconut diethanolamide | 2 g |
| Oxyethylenated nonylphenol containing 9 mol of ethylene oxide | 8 g |
| 2-Amino-2-methyl-1-propanol qs | pH 9 |
| Water qs | 100 g |

The experimental procedure was identical to that of Example 1. The luminance L of the two types of hair treated with vapour was subsequently measured (measurements were made using a MINOLTA CHROMA METER CR 200 colorimeter).

The difference: L natural—L permanent waved, (ΔL), which represents the selectivity, was equal to 3.2.

EXAMPLE 6 (comparative)

The same composition as that of Example 5 was used. The experimental procedure was identical to that of Example 2.

The luminance L of the two types of hair was subsequently measured (measurements were made using a MINOLTA CHROMA METER CR 200 colorimeter).

The difference: L natural—L permanent waved, (ΔL), which represents the selectivity, was equal to 9.5: it was three times as high as that obtained with the process according to the invention (Ex. 5).

EXAMPLE 7 (invention)

A composition having the following characteristics was used:

| | |
|---|---|
| 1-Hydroxy-2-amino-3-nitrobenzene | 0.5 g |
| Propylene glycol monomethyl ether | 10 g |
| Coconut diethanolamide | 2 g |
| Oxyethylenated nonylphenol containing 9 mol of ethylene oxide | 8 g |
| 2-amino-2-methyl-1-propanol qs | pH 9 |
| Water qs | 100 g |

The experimental procedure was identical to that of Example 1. The luminance L of the two types of hair treated with vapour was subsequently measured (measurements were made using a MINOLTA CHROMA METER CR 200 colorimeter).

The difference: L natural—L permanent waved, ($\Delta L$), which represents the selectivity, was equal to 0.7.

EXAMPLE 8 (comparative)

The same composition as that of Example 7 was used. The experimental procedure was identical to that of Example 2. The luminance L of the two types of hair was subsequently measured (measurements were made using a MINOLTA CHROMA METER CR 200 colorimeter).

The difference: L natural—L permanent waved, ($\Delta L$), which represents the selectivity, was equal to 2.7: it was much higher than that obtained with the process according to the invention (Ex. 7).

EXAMPLE 9 (comparative)

A composition having the following characteristics was used (not in accordance with the invention):

| | |
|---|---|
| 2-Nitro-para-phenylenediamine | 0.5 g |
| Propylene glycol monomethyl ether | 10 g |
| Coconut diethanolamide | 2 g |
| Oxyethylenated nonylphenol containing 9 mol of ethylene oxide | 8 g |
| 2-Amino-2-methyl-1-propanol qs | pH 9 |
| Water qs | 100 g |

A lock of natural hair and a lock of the same hair permanent waved was dyed according to the experimental procedure of Example 1 (water vapour 90° C.—30 seconds twice). The difference: L natural—L permanent waved, ($\Delta L$), which represents the selectivity, was equal to 1.9.

A lock of natural hair and a lock of the same hair permanent waved were subsequently dyed with the same composition as above, according to the experimental procedure of Example 2 (room temperature, 30 minutes).

The difference: L natural—L permanent waved, ($\Delta L$) which represents the selectivity, was equal to 1.6. With this type of dye composition, which did not fall within the scope of the invention, the selectivity was not decreased with a vapour treatment in accordance with the invention.

What is claimed is:

1. A process for the direct dyeing of keratinous fibres to lower selectivity thereon, comprising the step of:

directly dyeing said fibres to lower said selectivity, said fibres having previously been contacted with a composition containing at least one direct dye selected from the 2-nitro-para-phenylene-diamine derivatives of formula (I) and the nitro aminophenol derivatives of formula (II):

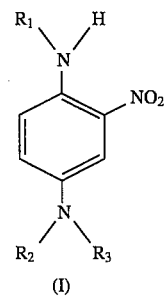
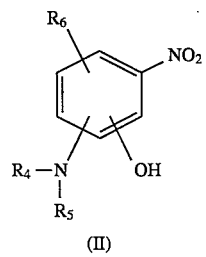

in which:

$R_1$ is selected from $C_1$-$C_4$ alkyl, $C_2$-$C_4$ monohydroxyalkyl, $C_2$-$C_4$ polyhydroxyalkyl radicals, $C_1$-$C_4$($C_1$-$C_4$ alkoxy) alkyl radicals and $C_1$-$C_4$ aminoalkyl radicals; $R_2$ and $R_3$ are selected from $C_1$-$C_4$ alkyl, $C_2$-$C_4$ monohydroxyalkyl and $C_2$-$C_4$ polyhydroxyalkyl radicals with the proviso that when one of $R_2$ or $R_3$ is $C_{1-4}$ alkyl, the other is $C_{2-4}$ monohydroxyalkyl or $C_{2-4}$ polyhydroxyalkyl; $R_4$ and $R_5$ are selected from hydrogen, $C_1$-$C_4$ alkyl, $C_2$-$C_4$ monohydroxyalkyl, $C_2$-$C_4$ polyhydroxyalkyl, and $C_1$-$C_4$ aminoalkyl radicals; and $R_6$ is selected from hydrogen, $C_1$-$C_4$ alkyl radicals, halogen atoms, and an $NO_2$ group, by contacting said fibres with a gas containing water vapour, the temperature of the gas being greater than 75° C., for a contact time between said gas and said fibres to be dyed of less than two minutes.

2. A process according to claim 1, wherein the gas has a temperature of at least 85° C.

3. A process according to claim 2, wherein the gas has a temperature ranging from 85° C. to 150° C.

4. A process according claim 1, wherein the gas is contacted with the fibres to be dyed for a period of time ranging from 0.01 second to less than 2 minutes.

5. A process according to claim 4, wherein the gas is contacted with the fibres to be dyed for a period of time ranging from 0.01 second to 30 seconds.

6. A process according to claim 5, wherein the gas is contacted with the fibres to be dyed for a period of time ranging from 1 second to 10 seconds.

7. A process according to claim 1, wherein the application of the gas is repeated several times on the fibres.

8. A process according to claim 1, wherein the gas exclusively contains water vapour.

9. A process according to claim 1, wherein the gas contains water vapour and at least one other compound in gas or vapour form.

10. A process according to claim 9, wherein the gas contains water vapour and air.

11. A process according to claim 1, wherein said at least one direct dye of formula (I) is selected from N,N',N'-tris(2'-hydroxyethyl)- 1,4-diamino-2-nitrobenzene, 1-methylamino-2-nitro-4-bis(2'-hydroxyethyl)aminobenzene, 1-methylamino-2-nitro-4-(N-methyl-N-2'-hydroxyethyl) aminobenzene, 1-(2'-aminoethyl)amino-2-nitro-4-bis(2'-hydroxyethyl) aminobenzene, 4-(N-ethyl-N-2'-hydroxyethyl)amino-1-(2'-hydroxyethyl)amino-2nitrobenzene, 1-(2'-methoxyethyl)amino-2-nitro-4-bis(2'-hydroxyethyl) aminobenzene, 1-(2',3'-dihydroxypropyl)amino-2-nitro-4-bis(2'-hydroxyethyl) aminobenzene, 1-(2',3'-dihydroxypropyl)amino-2-nitro-4-(N-methyl-N-2'-hydroxyethyl)aminobenzene, 1-(2',3'-dihydroxypropyl)amino-2-nitro-4-(N-ethyl-N-2'-hydroxyethyl)aminobenzene and 1-methylamino-2-nitro-4-(N-methyl-N-2',3'-dihydroxypropyl)aminobenzene.

12. A process according to claim 1, wherein said at least one direct dye of formula (II) is selected from 3-amino-4-hydroxynitrobenzene, 3-hydroxy-4-aminonitrobenzene, 2-hydroxy-3-amino-1,5-dinitrobenzene, 2-hydroxy-5-aminonitrobenzene, 1-hydroxy-3-nitro-4-N-(2'-hydroxyethyl)aminobenzene, 1-hydroxy-2-amino-3-nitrobenzene, 1-amino-2-nitro-4-hydroxy-5-methylbenzene, 1-N-(2'-hydroxyethyl)amino-2-hydroxy-4-nitrobenzene, 1-hydroxy-2-N-(2'-hydroxyethyl)amino-4,6-dinitrobenzene, 2-chloro-6-N-ethylamino-1-hydroxy-4-nitrobenzene, 6-chloro-4-nitro-2-aminophenol 1-hydroxy-3-nitro-4-N-(3'-hydroxypropyl)aminobenzene, 1-hydroxy-2-N,N-(2'-hydroxyethyl)amino-5-nitrobenzene, 2-amino-4-hydroxy-1-nitrobenzene, 2-hydroxy-4-amino-1-nitrobenzene, 1-hydroxy-3-nitro-4-aminobenzene, 2-hydroxy-5-N-(2'-hydroxyethyl)amino-1-nitrobenzene, 2-hydroxy-6-amino-1-nitrobenzene, 2-hydroxy-3-amino-1-nitrobenzene, 2-hydroxy-3-chloro-6-amino-1-nitrobenzene, 2-N-(2'-hydroxyethyl)amino-3-hydroxy-1-nitrobenzene, 3-N-(2'-hydroxyethyl)amino-4-hydroxy-1-nitrobenzene, 2-hydroxy-6-N-(2'-hydroxyethyl)amino-1-nitrobenzene, 1-hydroxy-2,6-dinitro-4-methylaminobenzene, 2-N-(2'-aminoethyl)amino-4-hydroxy-1-nitrobenzene, 3-hydroxy-4-N-(2'aminoethyl)amino-1-nitrobenzene and 2-N-(2'-hydroxyethylamino)-4-hydroxy-1-nitrobenzene.

13. A process according to claim 1, wherein said at least one direct dye is present in concentrations ranging from 0.01% to 10% by weight relative to the total weight of the composition.

14. A process according to claim 1, wherein the composition containing at least one direct dye has a pH ranging from 2 to 11.

15. A process according to claim 1, wherein said keratinous fibres are human keratinous fibres.

16. A process for the direct dyeing of keratinous fibres to lower selectivity thereon, comprising the step of:

directly dyeing said fibres to lower said selectivity, by contacting said fibres (1) with a composition containing at least one direct dye selected from the 2-nitro-paraphenylenediamine derivatives of formula (I) and the nitro aminophenol derivatives of formula (II):

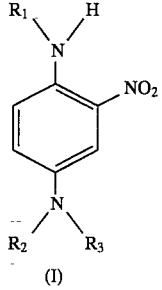 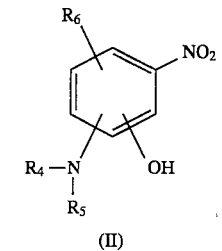

in which:

$R_1$ is selected from $C_1$-$C_4$ alkyl, $C_2$-$C_4$ monohydroxyalkyl, $C_2$-$C_4$ polyhydroxyalkyl radicals, $C_1$-$C_4$($C_1$-$C_4$ alkoxy) alkyl radicals and $C_1$-$C_4$ aminoalkyl radicals; $R_2$ and $R_3$ are selected from $C_1$-$C_4$ alkyl, $C_2$-$C_4$ monohydroxyalkyl and $C_2$-$C_4$ polyhydroxyalkyl radicals with the proviso that when one of $R_2$ or $R_3$ is $C_{1-4}$ alkyl, the other is $C_{2-4}$ monohydroxyalkyl or $C_{2-4}$ polyhydroxyalkyl; $R_4$ and $R_5$ are selected from hydrogen, $C_1$-$C_4$ alkyl, $C_2$-$C_4$ monohydroxyalkyl, $C_2$-$C_4$ polyhydroxyalkyl, and $C_1$-$C_4$ aminoalkyl radicals; and $R_6$ is selected from hydrogen, $C_1$-$C_4$ alkyl radicals, halogen atoms, and an $NO_2$ group; and (2) with a gas containing water vapour, the temperature of the gas and the contact time between said gas and said fibres being sufficient to lower said selectivity.

17. A process according to claim 16, wherein said keratinous fibres are human keratinous fibres.

18. A process for the direct dyeing of keratinous fibres to lower selectivity thereon, comprising the step of:

directly dyeing said fibres to lower said selectivity, by contacting said fibres (1) with a composition containing at least one direct dye selected from the 2-nitro-paraphenylenediamine derivatives of formula (I) and the nitro aminophenol derivatives of formula (II):

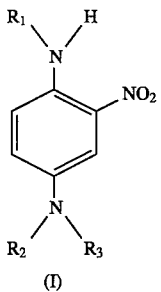 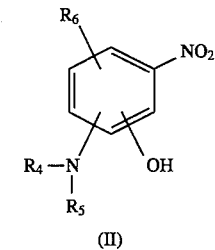

in which:

$R_1$ is selected from $C_1$-$C_4$ alkyl, $C_2$-$C_4$ monohydroxyalkyl, $C_2$-$C_4$ polyhydroxyalkyl radicals, $C_1$-$C_4$($C_1$-$C_4$ alkoxy) alkyl radicals and $C_1$-$C_4$ aminoalkyl radicals; $R_2$ and $R_3$ are selected from $C_1$-$C_4$ alkyl, $C_2$-$C_4$ monohydroxyalkyl and $C_2$-$C_4$ polyhydroxyalkyl radicals with the proviso that when one of $R_2$ or $R_3$ is $C_{1-4}$ alkyl, the other is $C_{2-4}$ monohydroxyalkyl or $C_{2-4}$ polyhydroxyalkyl; $R_4$ and $R_5$ are selected from hydrogen, $C_1$-$C_4$ alkyl, $C_2$-$C_4$ monohydroxyalkyl, $C_2$-$C_4$ polyhydroxyalkyl, and $C_1$-$C_4$ aminoalkyl radicals; and $R_6$ is selected from hydrogen, $C_1$-$C_4$ alkyl radicals, halogen atoms, and an $NO_2$ group; and (2) with a gas containing water vapour, the temperature of said gas being at least 75° C. and the contact time between said gas and said fibres being sufficient at said temperature to lower said selectivity.

19. A process according to claim 18, wherein said keratinous fibres are human keratinous fibres.

20. A process for the direct dyeing of keratinous fibres to lower selectivity thereon, comprising the step of:

directly dyeing said fibres to lower said selectivity, by contacting said fibres (1) with a composition containing at least one direct dye selected from the 2-nitro-para-phenylenediamine derivatives of formula (I) and the nitro aminophenol derivatives of formula (II):

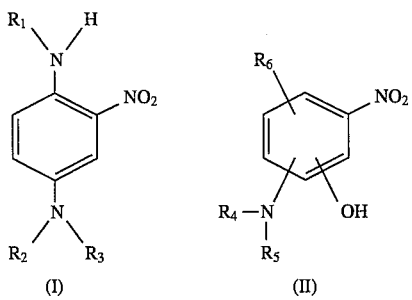

in which:
$R_1$ is selected from $C_1$-$C_4$ alkyl, $C_2$-$C_4$ monohydroxyalkyl, $C_2$-$C_4$ polyhydroxyalkyl radicals, $C_1$-$C_4$($C_1$-$C_4$ alkoxy) alkyl radicals and $C_1$-$C_4$ aminoalkyl radicals; $R_2$ and $R_3$ are selected from $C_1$-$C_4$ alkyl, $C_2$-$C_4$ monohydroxyalkyl and $C_2$-$C_4$ polyhydroxyalkyl radicals with the proviso that when one of $R_2$ or $R_3$ is $C_{1-4}$ alkyl, the other is $C_{2-4}$ monohydroxyalkyl or $C_{2-4}$ polyhydroxyalkyl; $R_4$ and $R_5$ are selected from hydrogen, $C_1$-$C_4$ alkyl, $C_2$-$C_4$ monohydroxyalkyl, $C_2$-$C_4$ polyhydroxyalkyl, and $C_1$-$C_4$ aminoalkyl radicals; and $R_6$ is selected from hydrogen, $C_1$-$C_4$ alkyl radicals, halogen atoms, and an $NO_2$ group; and (2) with a gas containing water vapour, for a time not exceeding two minutes, and wherein said gas has a sufficient temperature for said time to lower said selectivity.

21. A process according to claim 20, wherein said keratinous fibres are human keratinous fibres.

22. A process for the direct dyeing of keratinous fibres to lower selectivity thereon, comprising the step of:

directly dyeing said fibres to lower said selectivity, by contacting said fibres (1) with a composition containing at least one direct dye selected from the 2-nitro-para-phenylenediamine derivatives of formula (I) and the nitro aminophenol derivatives of formula (II):

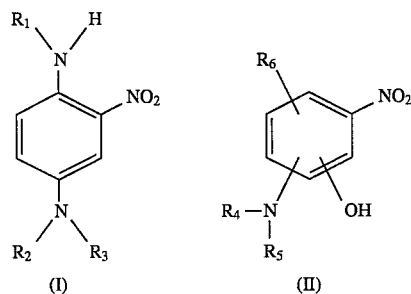

in which:
$R_1$ is selected from $C_1$-$C_4$ alkyl, $C_2$-$C_4$ monohydroxyalkyl, $C_2$-$C_4$ polyhydroxyalkyl radicals, $C_1$-$C_4$($C_1$-$C_4$ alkoxy) alkyl radicals and $C_1$-$C_4$ aminoalkyl radicals; $R_2$ and $R_3$ are selected from $C_1$-$C_4$ alkyl, $C_2$-$C_4$ monohydroxyalkyl and $C_2$-$C_4$ polyhydroxyalkyl radicals with the proviso that when one of $R_2$ or $R_3$ is $C_{1-4}$ alkyl, the other is $C_{2-4}$ monohydroxyalkyl or $C_{2-4}$ polyhydroxyalkyl; $R_4$ and $R_5$ are selected from hydrogen, $C_1$-$C_4$ alkyl, $C_2$-$C_4$ monohydroxyalkyl, $C_2$-$C_4$ polyhydroxyalky, and $C_1$-$C_4$ aminoalkyl radicals; and $R_6$ is selected from hydrogen, $C_1$-$C_4$ alkyl radicals, halogen atoms, and an $NO_2$ group; and (2) with a gas containing water vapour, the temperature of said gas being at least 75° C., for a contact time between said gas and said fibres not exceeding two minutes.

23. A process according to claim 22, wherein said keratinous fibres are human keratinous fibres.

24. A process according to claim 22, wherein said gas containing water vapour is contacted with said fibres subsequent to said fibres being contacted with a composition containing at least one direct dye of formula (I) or of formula (II).

25. A process according to claim 22, wherein said gas containing water vapour is contacted with said fibres simultaneously with said fibres being contacted with a composition containing at least one direct dye of formula (I) or of formula (II).

26. A process according to claim 1, wherein said gas has a temperature ranging from 75° C. to less than 100° C.

27. A process according to claim 26, wherein said gas has a temperature ranging from 85° C. to less than 100° C.

28. A process according to claim 27, wherein said gas has a temperature ranging from 90° C. to less than 100° C.

* * * * *